United States Patent
Maincent et al.

(10) Patent No.: US 8,052,998 B2
(45) Date of Patent: Nov. 8, 2011

(54) PARTICULATE VECTORS FOR IMPROVING ORAL ABSORPTION OF ACTIVE PRINCIPLES

(75) Inventors: Philippe Maincent, Nancy (FR); Nathalie Ubrich, Nancy (FR); Claude Vigneron, Nancy (FR)

(73) Assignee: Laboratorios Farmaceuticos Roui, S.A., Madrid (ES)

( * ) Notice: Subject to any disclaimer, the term of this patent is extended or adjusted under 35 U.S.C. 154(b) by 670 days.

(21) Appl. No.: 10/332,351

(22) PCT Filed: Jul. 5, 2001

(86) PCT No.: PCT/FR01/02159
§ 371 (c)(1),
(2), (4) Date: Jan. 8, 2003

(87) PCT Pub. No.: WO02/03960
PCT Pub. Date: Jan. 17, 2002

(65) Prior Publication Data
US 2005/0013866 A1   Jan. 20, 2005

(30) Foreign Application Priority Data
Jul. 7, 2000   (FR) ..................... 00 08902

(51) Int. Cl.
*A61K 9/14*   (2006.01)
*A61K 9/50*   (2006.01)

(52) U.S. Cl. .............. 424/489; 424/499; 424/500
(58) Field of Classification Search .......... 424/489–494, 424/465, 466, 480
See application file for complete search history.

(56) References Cited

U.S. PATENT DOCUMENTS

| | | | | |
|---|---|---|---|---|
| 5,151,273 A | * | 9/1992 | Korsatko-Wabnegg et al. | 424/465 |
| 5,490,990 A | * | 2/1996 | Grabowski et al. | 424/486 |
| 5,622,657 A | * | 4/1997 | Takada et al. | 264/4.32 |
| 5,629,011 A | * | 5/1997 | Illum | 424/434 |
| 5,686,113 A | * | 11/1997 | Speaker et al. | 424/490 |

FOREIGN PATENT DOCUMENTS

| | | |
|---|---|---|
| FR | 2 769 853 | 4/1999 |
| WO | WO 92 11844 | 7/1992 |
| WO | WO 9211844 A1 * | 7/1992 |
| WO | WO 94 14420 | 7/1994 |
| WO | WO 96/28143 | 9/1996 |
| WO | WO 0028989 A1 * | 5/2000 |
| WO | WO 0043044 A1 * | 7/2000 |

* cited by examiner

*Primary Examiner* — Michael G Hartley
*Assistant Examiner* — Micah-Paul Young
(74) *Attorney, Agent, or Firm* — Rick Matos; Innovar, L.L.C.

(57) ABSTRACT

The invention concerns particulate vectors designed to improve oral absorption of active principles, characterized in that they consist of a polymeric matrix comprising at least a biodegradable polymer associated with at least a polycationic polymer.

15 Claims, 4 Drawing Sheets

PARTICULATE VECTORS FOR IMPROVING ORAL ABSORPTION OF ACTIVE PRINCIPLES

This application is the U.S. national phase of international application PCT/FR01/02159 filed Jul. 5, 2001 which designated the U.S.

The present invention relates to particulate vectors for increasing the absorption of active principles after oral administration to man or animals.

It is currently accepted that most of the active principles that will be used in the next 30 years have not yet been discovered. Furthermore, the prospective studies are in agreement in thinking that the majority of these future active principles, derived from biological engineering techniques, will be peptides and/or proteins. These new drugs will be extremely active with effective doses that will be of the order of a microgram or less. A few drugs, mainly peptides, are already on the North American or European market (LH/RH analogs, growth hormone, streptokinase, antibodies, etc.). More than one hundred peptides and proteins are currently undergoing clinical trials on humans.

The peptides and proteins currently on the market have a certain number of drawbacks that limit their use in humans:
the only route of administration is the parenteral route (intravenous, subcutaneous or intramuscular) and
their half-life for elimination in the body is short, thus necessitating multiple administrations.

No pharmaceutical forms currently exist for the oral administration of peptides and proteins, whereas multiparticulate forms, intended for the parenteral route, have been present on the market for several years (Enantone® from the Takeda laboratories, and Sandostatine® from the Novartis laboratories).

The absence of forms intended for the oral route is explained by the sensitivity of peptides and proteins to the digestive juices, which degrade protein-based medicinal products in the same way as food proteins; this results in a virtually total absence of absorption due to the initial destruction. Since the oral route is the route that is the most common and the most easily accepted in man, the development of a form for protecting peptides and proteins from inactivation by the digestive juices while at the same time allowing gastrointestinal absorption would represent major therapeutic progress for the start of this century.

It is on account of this inactivation by the proteolytic enzymes of the gastrointestinal tract that insulin, a peptide of 51 amino acids, has been administered parenterally for almost 80 years. Certain attempts to improve the oral absorption of peptides and proteins have been made. Several literature studies cite, for example, an increase in the oral absorption of insulin when it is incorporated into poly(isobutyl cyanoacrylate) nanocapsules (Michel C., et al., J. Pharm. Pharmacol., 43, (1991), 1-5; Damge C., et al., Diabetes, 37, (1988), 246-251). These nanocapsules have a vesicular structure corresponding to nanodroplets of oil surrounded by a very thin membrane of the polymer. However, the polymer chosen is known for its toxic nature on cells, which prevents a repeated administration over several years from being envisioned. Similarly, the presence of oil in the core of the nanocapsules would, in the long term, pose problems of toxicity at the sites of administration, hence preventing the marketing of insulin nanocapsules from being envisioned. Furthermore, the hypoglycemiant effect is observed only after 2 days, probably due to very limited passage of the particles across the intestinal mucosae and a slow release of insulin. Insulin nanoparticles prepared with the same polymer (polyalkyl cyanoacrylate) and administered orally have not shown any hypoglycemiant activity (Couvreur P. et al., Acta Pharm, Technol., 26, (1980), 220-222).

Similarly, the oral administration of cyclosporin is erratic and eminently variable despite the development of a microemulsion pharmaceutical form (Neoral®, from the Novartis laboratories). The development of cyclosporin nanoparticles has not currently made it possible to increase the oral bioavailability of this active principle, which remains limited to less than 5% (Ford J. et al., Int. J. Pharm., 183, (1999), 3-6).

Heparin has been used for about fifty years in the prevention and treatment of thromboembolic disease, but has the drawback of being particularly hemorrhagic and of requiring strict biological and clinical monitoring. Besides functional anomalies of hemostasis which lead to a situation of hypercoagulability (congenital or acquired deficit of anti-thrombin III, cofactor II, proteins C and S), various risk factors are noted for thromboembolic disease, defined as a set of hemostasis disorders leading to the formation of a fibrin clot or platelet plugs in the lumen of a blood vessel.

These patient-related risk factors are:
age: the disease reaches more than 50% in individuals over 40 years old
sex: higher incidence of the disease in women under 40, and especially during pregnancy
obesity
the taking of contraceptive agents
smoking
arterial hypertension
diabetes
hypercholesterolemia
confinement to bed, which promotes stasis
varices
cardiac insufficiency
surgery: the incidence of the disease increases in the post-surgical state.

Heparin is a natural sulfated anionic mucopoly-saccharide consisting of D-glucosamine and glucuronic acid or iduronic acid saccharide units, which is synthesized by the mastocytes and extracted industrially from bovine lung or pig intestine. Since glucosamines and uronic acids may be substituted with sulfate or acetyl groups, about ten different saccharide units have thus been identified. These various units are distributed very coherently, defining three intramolecular regions, one of which is a pentasaccharide structure, the site of action between heparin and antithrombin III. On binding to antithrombin III, heparin catalyzes the inactivation of several clotting factors, in particular thrombin and factor Xa. This results in a prolongation of the clotting time measured by the activated cephalin time. Heparin is in fact a highly heterogeneous substance since it comprises a mosaic of saccharide-chain molecules with a molecular weight of between 2 500 and 40 000 daltons. The polysaccharide chains of natural heparin may be fractionated by various processes (chromatography or chemical and enzymatic hydrolysis), thereby producing low molecular weight heparins (LMWHs) that have novel properties which distinguish them from unfractionated heparin. For those skilled in the art, the most important properties are a half-life that is about twice as long, little or no anticoagulant effect, greater ease of subcutaneous administration, better local tolerability, low hemorrhagic power and longer pharmacokinetics.

Heparin is currently administered parenterally, i.e. intravenously or subcutaneously. However, this type of administration is restrictive and may pose problems of patient compliance. Furthermore, once injected intravenously, heparin is rapidly eliminated from the blood circulation, and a large dose must be administered at regular intervals in order to obtain effective anticoagulant action, which is often accompanied by abnormal bleeding or complications such as thrombopenia.

Thus, the possibility of administering heparin orally would in fact have a major impact in a good number of clinical cases in the cardiovascular field.

Now, on the basis of its structure, heparin is seen to be a molecule of high molecular weight comprising a high charge density. It therefore cannot easily cross the digestive barrier after oral administration.

Thus, orally-administered heparin is not absorbed in the gastrointestinal tract, and loses its anticoagulant activity in acidic medium (Morton et al., Int. J. Pharm., 9, (1981), 321-335, Doutremepuich et al., Seminars in Thrombosis and Hemostasis, 11 (3), (1985), 323-325). The strategy therefore used consisted in making up for the lack of absorption/anticoagulant activity by means of a large increase in the administered dose.

Thus, previous studies have demonstrated that, after oral administration to man of a large amount of heparin in solution (40 000 IU, i.e. between 10 and 17 times the dose conventionally administered intravenously every two hours), only a small amount is absorbed via the digestive system and distributed in the blood. Furthermore, the anticoagulant activity measured by means of the activated cephalin time (ACT) is very low (Baughman et al., Circulation, 16, (1998), 1610-1615). Similarly, in man, after oral administration of low molecular weight heparin (LMWH), no activity is observed in the plasma (Dryjski et al., Br. J. Clin. Pharmacol., 2, (1989), 188-192).

Numerous chemical modifications to heparin and the preparation of various formulations have been envisioned to improve the bioavailability of heparin after oral administration.

First, tests consisted in studying modifications of the heparin structure (heparins of different sources, more or less fragmented, up to the appearance of the low molecular weight heparins).

Solutions were prepared by complexing heparin with adjuvants such as lysine, spermine or glycine, so as to reduce the ionization of heparin. After oral administration, these solutions showed low absorption of the heparin (Tidball et al., Proc. Soc. Exp. Biol. Med. 111, (1962), 713-715).

Solutions of acid salts of heparin were also prepared by combining heparin with sodium salts of ethylene-diaminetetraacetic acid or bile salts (Morton et al., Int. J. Pharm., 9, (1981), 321-335).

Oil-in-water (O/W) emulsions or micellar solutions of monoolein salts intended for increasing the absorption of heparin were also envisioned (Taniguchi et al., Int. J. Pharm., 4, (1980), 219-228).

Solutions of propylene glycol containing heparin and compounds derived from the N-acylation of the aromatic amino acid 4-aminophenylbutyric acid demonstrated an improvement in the gastrointestinal absorption and the bioavailability of heparin after oral administration to rats and monkeys (Leone-Bay et al., J. Controlled Red., 50, (1998), 41-49).

Although most of these various heparin solutions (Tidball et al., Proc. Soc. Exp. Biol. Med. 111, (1962), 713-715, Morton et al., Int. J. Pharm., 9, (1981), 321-335, Taniguchi et al., Int. J. Pharm., 4, (1980), 219-228 and Leone-Bay et al., J. Controlled Red., 50, (1998), 41-49) have made it possible to improve the gastrointestinal absorption of heparin, the anticoagulant effect observed is much smaller and of shorter duration than that obtained after subcutaneous administration for very much greater doses. Furthermore, the toxicopharmacological status of the absorption promoters and excipients used compromises the success of these formulations.

Gastroresistant heparin gel capsules were administered to rabbits and small plasmatic anti-Xa activity (0.15 IU/ml) is observed between the 2nd and the 4th hour. However, in this case also, very large doses of heparin (15 000 IU anti-Xa/kg) are administered (Doutremepuich et al., Thèrapie, 39, (1984), 147-152).

Other studies have consisted in seeking to optimize the absorption of heparin, and, as a result, the desired therapeutic effect. This novel step was marked by the manufacture of drug administration systems, such as liposomes and microparticles, which enabled the encapsulation of heparin to be envisioned. These encapsulation techniques used for enzymes, drugs and hormones allow these molecules to remain in the blood circulation for longer than when they are used in free form, on account of their gradual release from the polymer systems and the protection that said systems impart to them with respect to enzymatic degradation (Couvreur et al., Drug Del. Rev., 10, (1993), 141-162).

Liposomes have also been prepared and administered to dogs; intestinal absorption of the active principle was observed, but only weak biological activity was detected, while doses of heparin that are still extremely high were administered (500 000 IU) (Ueno et al., Chem. Pharm. Bull., 30 (6), (1982), 2245-2247).

Finally, microspheres composed of heat-condensed amino acids have also been developed (Santiago et al., Proceed. Intern. Symp. Control. Rel. Mater., 19, (1992), 514-515 and Santiago et al., Proceed. Intern. Symp. Control. Rel. Bioact. Mater., 20, (1993), 300-301). In the latter case, the particle obtained, which is between 0.5 and 10 µm in size, is referred to as a proteinoid. Their oral administration to rats and monkeys made it possible to determine intestinal absorption of the heparin; however, these promising results come up against three major obstacles. Firstly, the biological activity of the heparin is only manifested for at most 90 minutes. Furthermore, the biological activity was obtained in rats for doses more than 10 times greater than those used parenterally in man. Finally, the very numerous current oral immunization studies are based on the phenomenon of uptake, by the Peyer plaques, of antigen-charged micro-particles that are between 1 and 10 µm in size. Under these conditions, the proteinoids used might induce an immunoallergic phenomenon that would compromise the repeated administration of these particles.

Polymer systems have also been the subject of many studies. Thus, Yang et al., (J. Control. Rel., 60, (1999), 269-277) prepared heparin microparticles based solely on polymers of lactic acid and of glycolic acid (PLGA) with the aim of inhibiting the proliferation of the smooth muscle cells of blood vessels during an in vitro study (Yang et al., J. Control. Rel., 60, (1999), 269-277). The microparticles, manufactured by a spray-drying technique, are very small (between 3 and 9 µm). The release of heparin in vitro is very slow (between 10 and 40 days), which is incompatible with an oral administration, for which the transit time is from about 24 to 48 hours.

However, all these tests use doses of heparin that are very much larger than that conventionally used therapeutically in man. Thus, there is still a need to provide patients with an administration system that increases the absorption of the active principles, especially of heparin, after oral administration and that allows said active principles to be administered at lower concentrations, thus reducing the harmful side effects.

Now, the inventors have shown, surprisingly and unexpectedly with regard to the permeation of large molecules across the gastrointestinal barrier, that particulate vectors comprising a polymer matrix based on a mixture of nonenteric biodegradable polymer and on a nonenteric polycationic polymer allow the oral administration of amounts of active principles, especially of heparin, that are close to those conventionally used parenterally.

Thus, one subject of the present invention is particulate vectors for improving the oral absorption of active principles, formed from a polymer matrix comprising at least one biodegradable polymer combined with at least one polycationic polymer.

For the purposes of the present invention, the biodegradable polymers and the polycationic polymers may or may not be gastroresistant (enteric).

In another particular embodiment of the invention, the polymer matrix is such that the percentage of the polycationic polymer ranges between 1% and 99% relative to the biodegradable polymer.

In another particular embodiment of the invention, the biodegradable polymer and the polycationic polymer are present in equivalent amount.

Advantageously, the nonenteric biodegradable polymer is chosen from the group consisting of polyesters, especially lactic acid polymers, copolymers of lactic acid and of glycolic acid (PLGA), poly-ε-caprolactone (PCL), polyanhydrides, poly(amides), poly(urethanes), poly(carbonates), poly(acetals), poly(ortho-esters) and natural polymers (collagen, polysaccharides, etc.).

Advantageously, the polycationic polymer is chosen from the group consisting of cellulose derivatives, the copolymers of acrylic and methacrylic acid esters sold by the company Rhöm GmbH under the name Eudragit® and more particularly methacrylic acid polyesters with a small proportion of trimethylammonioethyl methacrylate chloride (Eudragit® RS) or a larger proportion of trimethylammonioethyl methacrylate chloride (Eudragit® RL), chitosan and its derivatives, and polylysine.

In one particularly advantageous mode of the invention, the biodegradable polymer is either PCL or PLGA, the molecular weight of said polymers being between 2 000 and 100 000.

In one particular embodiment according to the invention, the particulate vectors are either in the form of nanoparticles between 50 and 1 000 nm and preferably between 200 and 400 nm in diameter, or in the form of microparticles between 1 and 1 000 µm and preferably between 50 and 200 µm in diameter.

According to the invention, the polymer matrix may also comprise one or more substances chosen from the group comprising enteric polymers, surfactants and water-soluble or liposoluble substances.

In one particular embodiment of the invention, the active principle is chosen from the group consisting of heparin and related products, low molecular weight heparins (LMWHs) and related products, peptides and proteins, especially insulin, cyclosporin, antisense oligonucleotides, DNA and growth hormone.

In another particular embodiment of the invention, the particulate vector for injecting standard heparin at a dose of between 2 000 IU and 20 000 IU/day and LMWH at a dose of between 600 IU and 4 200 IU/day [sic].

A subject of the present invention is also a pharmaceutical composition containing a particulate vector as described above, in combination with any pharmaceutically acceptable excipient.

The compositions may be used one or more times a day, in any form that is suitable for oral administration, especially in the form of gel capsules, tablets, granules, sachets or lyophilizate.

The compositions according to the invention allow the active principles to be administrated at doses equivalent to about 1 to 10 times the dose used parenterally. Such vectors make it possible to eliminate the drawbacks of the parenteral route (sterilization of the drug, pain at the point of injection, patient anxiety, risk of infection, limited number of injection points). They also avoid, as is often the case via the oral route, the administration of very large doses of active principles since the active principles are used at a dose equivalent to that conventionally used intravenously or very slightly higher, at most 10 times and preferably 1 to 3 times said dose.

Moreover, the use of polymers considered as biocompatible (biodegradable and/or nonbiodegradable) is a guarantee of absence of toxicity of said particles.

The particulate vectors according to the invention also make it possible, unexpectedly, to obtain longer action than for the administration of a similar dose in solution administered intravenously, whereas it is known that the doses administered orally must often be very much higher than the doses administered intravenously in order to be able to exert their activity, on account of the losses of active principle incurred by their residence in the gastrointestinal tract (acidic pH of the stomach, enzymes, various secretions, first passage through the liver, etc.).

In accordance with the invention, the particulate vectors may be prepared by any method known to those skilled in the art. Examples that may be mentioned include the method of preparation by emulsification and solvent evaporation as described by Alex et al., (J. Microencapsulation, 7 (3), (1990), 347-355). Other methods may also be envisioned, especially spray-drying, coating and extrusion.

The examples and figures that follow illustrate the invention without, however, limiting it.

EXAMPLE 1

Figure 1:
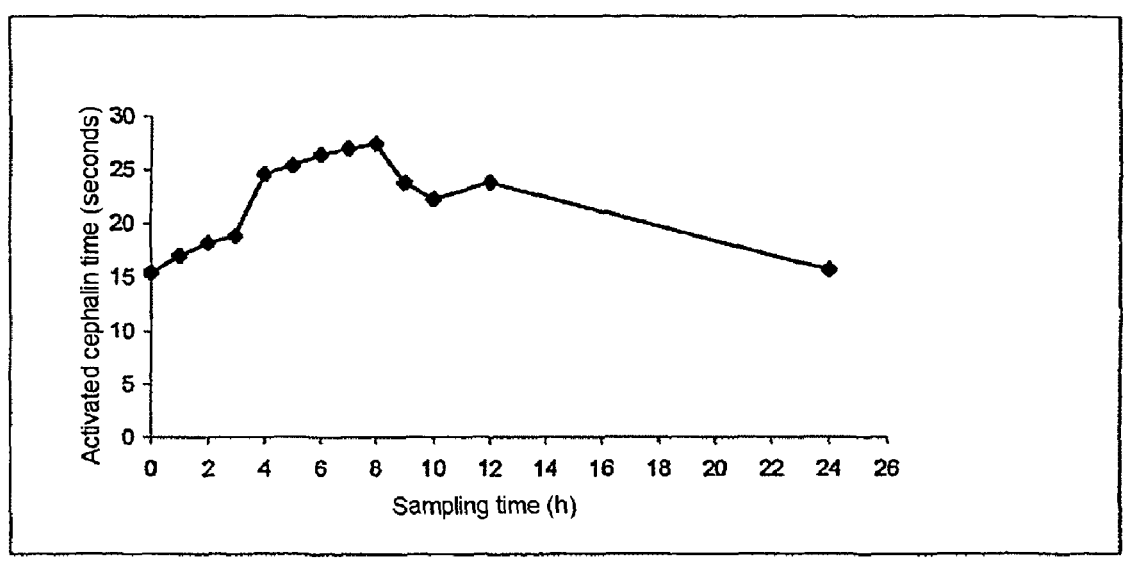
FIG. 1 illustrates the biological activity of heparin determined by the activated cephalin time after oral administration of heparin microparticles prepared from the polymer mixture Eudragit® RS/PLGA in proportions of (1/1) according to the procedure of example 1 and administered according to the procedure of example 9.

Preparation of Particulate Vectors Containing Heparin (Microparticles)

A solution of standard or low molecular weight heparin (1 ml, 5 000 IU) is emulsified with magnetic stirring for 3 minutes (500 rpm) in a solution of dichloro-methane (10 ml) containing the polymer or the polymer mixture (250 mg). This first emulsion (water/oil) is then poured into a volume of water (1 500 ml) containing a surfactant, polyvinyl alcohol (0.1% degree of hydrolysis 88%), which gives, by mechanical stirring (2 000 rpm), a second water/oil/water emulsion. After stirring for 2 hours, precipitation of the dispersed droplets is obtained after evaporating off the solvent. The polymer microparticles thus obtained are then isolated by filtration. The particles have a mean size of 150 μm.

EXAMPLE 2

Preparation of Particulate Vectors Containing Heparin and Gelatin A (Microparticles)

The process is performed according to example 1, with addition of gelatin A (0.5%) to the heparin solution.

EXAMPLE 3

Preparation of Particulate Vectors Containing Heparin and Sodium Chloride (Microparticles)

The process is performed according to example 1, with addition of NaCl (0.2%) to the heparin solution.

EXAMPLE 4

Preparation of Particulate Vectors Containing Heparin (Nanoparticles)

A solution of standard or low molecular weight heparin (1 ml, 5 000 IU) is emulsified using an ultrasound probe for 3 minutes in a solution of dichloromethane (10 ml) containing the polymer or the polymer mixture (250 mg). This first emulsion (water/oil) is then poured into a volume of water (200 ml) containing a surfactant, polyvinyl alcohol (0.1%), which gives, by homogenization under pressure (two-stage homogenizer), a second water/oil/water emulsion. After shear for 3 minutes, the stirring is stopped and the solvent is evaporated from the colloidal suspension in an evaporator under reduced pressure, resulting in the formation of polymer nanoparticles in suspension in water. The nanoparticle suspension is washed 3 times by centrifugation (25 000 g). This suspension may be used as obtained or freeze-dried. The particles have a mean size of 250 nm.

EXAMPLE 5

Preparation of Particulate Vectors Containing Heparin and Gelatin A (Nanoparticles)

The process is performed according to example 4, with addition of gelatin A (0.5%) to the heparin solution.

EXAMPLE 6

Preparation of Particulate Vectors Containing Heparin and Sodium Chloride (Nanoparticles)

The process is performed according to example 4, with addition of NaCl (0.2%) to the heparin solution.

EXAMPLE 7

Physicochemical Characterization of the Particles

Microparticles and nanoparticles are prepared according to the procedures of examples 1 to 6 and contain in total 0.25 g of polymers or of polymer mixture.

The characteristics of the microparticles are collated in table 1, as the mean of 3 tests (mean±standard deviation).

The characteristics of the nanoparticles are collated in table 2, as the mean of 4 tests (mean±standard deviation).

The content of active principle (expressed as a percentage and as IU of heparin/gram of polymer) in and/or on said particles is determined by means of a colorimetric method validated with a solution of Azure II in the case of unfractionated standard heparin, and by nephelometry in the case of LMWH (low molecular weight heparin).

The diameter of the microparticles and nanoparticles was obtained by the standard means of light scattering/diffusion known to those skilled in the art. The surface potential of the nanoparticles was determined by laser electrophoresis.

The results show that the manufacturing technique is very reproducible.

For the microparticles and nanoparticles prepared with a biodegradable polymer alone, the levels of incorporation of heparin are low, which would require, even assuming absorption, excessively large and incompatible amounts of particles (of the order of several grams in a single administration).

In contrast, the microparticles according to the invention have a level of incorporation that is sufficient to allow the administration of compatible amounts of particles.

TABLE 1

| Type of polymer<br>Amount = 0.25 g | Level of incorporation | | Mean size (μm) |
|---|---|---|---|
| | % | IU/g of polymer | |
| Eudragit ®RS PO[a] | 49.29 ± 4.03 | 9952 ± 798.1 | 96.23 |
| Eudragit ® RL PO[a] | 79.89 ± 3.45 | 15956 ± 687.6 | 79.76 |
| PCL[a] | 23.55 ± 3.51 | 4566 ± 699.7 | 128.33 |
| PLGA[a] | 26.81 ± 3.76 | 1929 ± 160.9 | 125.16 |
| PCL/PLGA (1/1)[a] | 17.52 ± 4.69 | 3506 ± 928.8 | 82.04 |
| RS/RL (1/1)[a] | 66.59 ± 1.54 | 13307 ± 303.1 | 88.07 |
| RS/RL/PLGA (1/1/2)[b] | 45.13 ± 2.85 | 8984 ± 568.7 | 71.07 |
| RS/PLGA (1/1)[b] | 52.48 ± 4.17 | 10517 ± 908.2 | 86.98 |
| RL/PLGA (1/1)[b] | 63.79 ± 3.95 | 12752 ± 785.3 | 128.51 |
| RS/RL/PCL (1/1/2)[b] | 40.39 ± 2.42 | 8126 ± 508.7 | 104.38 |
| RS/PCL (1/1)[b] | 36.27 ± 3.72 | 7277 ± 722.0 | 129.36 |
| RL/PCL (1/1)[b] | 45.16 ± 2.13 | 9032 ± 466.7 | 103.45 |
| RS/gelatin A (5%)[a] | 66.63 ± 4.06 | 13323 ± 811.2 | 123.64 |
| RS/NaCl (2%)[a] | 16.40 ± 2.41 | 3186 ± 394.6 | 84.99 |
| RS/gelatin B (5%)[a] | 46.31 ± 1.54 | 9260 ± 299.9 | 80.40 |
| PCL/gelatin A (5%)[a] | 57.96 ± 4.73 | 11577 ± 928.4 | 201.04 |
| PCL/NaCl (2%)[a] | 17.09 ± 1.90 | 3416 ± 377.5 | 90.89 |
| PCL/gelatin B (5%)[a] | 24.08 ± 2.72 | 4826 ± 536.7 | 124.96 |
| PLGA/gelatin A (5%)[a] | 58.71 ± 3.94 | 11735 ± 786.8 | 282.24 |
| PLGA/NaCl (2%)[a] | 22.59 ± 3.34 | 4517 ± 666.1 | 107.97 |
| PLGA/gelatin B (5%)[a] | 37.51 ± 2.41 | 7505 ± 491.6 | 130.43 |

[a] comparative examples
[b] examples according to the invention

TABLE 2

| Type of polymer Amount = 0.25 g | Encapsulated heparin in IU/g of polymer (%) | Surface potential (mV) | Size (nm) (polydispersity) |
|---|---|---|---|
| Eudragit ®RL[a] | 19477 ± 490.2 (97.38 ± 2.45) | −38.8 ± 2.4 | 265.7 ± 8.22 (0.102) |
| Eudragit ®RS[a] | 11825 ± 139.6 (59.13 ± 0.71) | −22.4 ± 0.45 | 268.5 ± 15.83 (0.110) |
| PCL[a] | 1673 ± 208.8 (8.36 ± 1.06) | −1.6 ± 0.22 | 285.3 ± 9.92 (0.064) |
| PLGA[a] | 2792 ± 800.5 (13.97 ± 4.01) | −4.5 ± 0.07 | 266.5 ± 4.00 (0.058) |
| RS/PLGA (1/1)[b] | 7101 ± 430.9 (35.53 ± 2.15) | −17.3 ± 1.35 | 273.4 ± 7.37 (0.083) |
| RL/PLGA (1/1)[b] | 9752 ± 720.8 (48.78 ± 3.60) | −37.2 ± 3.30 | 268.9 ± 8.13 (0.10) |
| RS/RL/PLGA[b] (1/1/2) | 7498 ± 138.4 (37.55 ± 0.69) | −30.7 ± 2.02 | 275.4 ± 3.41 (0.074) |
| RS/PCL (1/1)[b] | 5657 ± 324.0 (28.30 ± 1.61) | −20.0 ± 0.67 | 285.9 ± 5.88 (0.07) |
| RL/PCL (1/1)[b] | 10663 ± 320.6 (53.36 ± 1.64) | −33.6 ± 1.93 | 303.6 ± 3.49 (0.086) |
| RS/RL/PCL (1/1/2)[b] | 7645 ± 588.4 (38.25 ± 2.94) | −29.9 ± 0.39 | 295.0 ± 4.34 (0.088) |
| RS/RL[a] | 14287 ± 448.3 (71.44 ± 2.21) | −35.7 ± 1.94 | 269.6 ± 7.07 (0.088) |
| PCL/PLGA[a] | 853 ± 158.4 (4.26 ± 0.79) | 2.5 ± 0.38 | 264.9 ± 0.61 (0.061) |
| RS/gelatin A[a] | 11891 ± 741.2 (59.43 ± 3.42) | −18.6 ± 1.21 | 279.9 ± 3.12 (0.099) |
| PCL/gelatin A[A] | 7414 ± 870.4 (37.04 ± 4.35) | −2.58 ± 0.23 | 284.4 ± 3.90 (0.091) |
| PLGA/gelatin A[a] | 8533 ± 701.7 (41.31 ± 3.51) | −4.4 ± 0.31 | 274.4 ± 3.22 (0.073) |

[a] comparative examples
[b] examples according to the invention

EXAMPLE 8

Amount of Heparin Released in vitro

The biological activity of heparin encapsulated in and then released from the particles prepared according to examples 1 to 6 was determined by means of a chronometric method (ACT, activated cephalin time; C. K. Prest® kit, Diagnostica Stago) and a chromogenic method (anti-Xa activity; Stachrom® Heparin kit, Diagnostica Stago) according to the manufacturer's instructions.

The results obtained show that the values obtained for the amount of heparin released are identical by the two methods, which confirms that the heparin has conserved its biological activity after encapsulation.

EXAMPLE 9

In Vivo Study After Oral Administration to Rabbits

Figure 2:
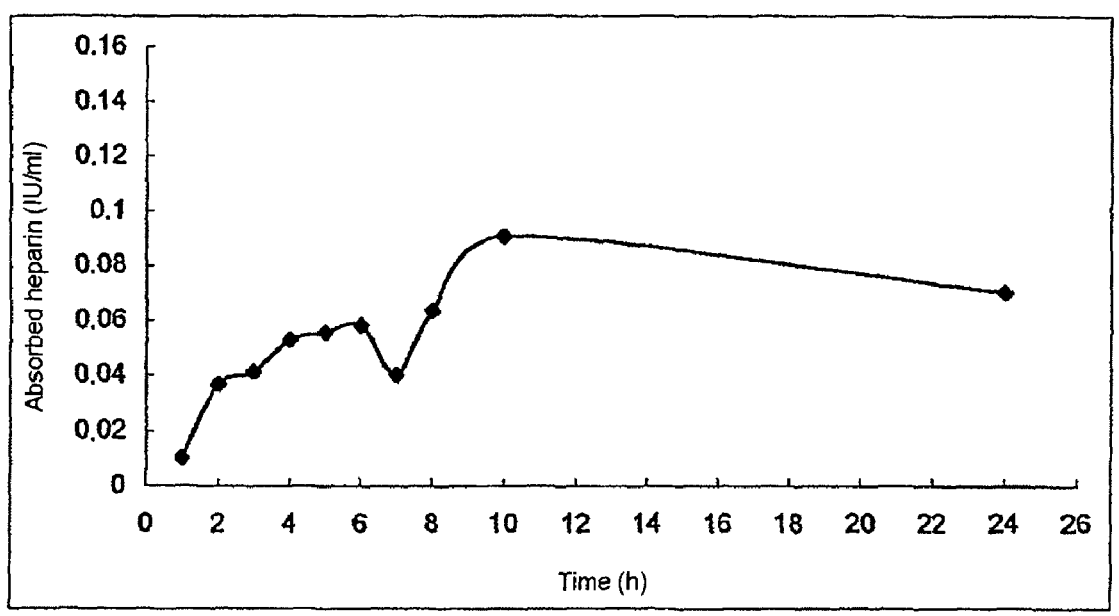
FIG. 2 illustrates the heparinemia after oral administration of heparin nanoparticles prepared from the polymer mixture Eudragit® RL/PCL in proportions of (1/1) according to the procedure of example 1 and administered according to the procedure of example 9.

The results are given in FIGS. 1 and 2.

Gel capsules containing the polymer particles of heparin prepared according to examples 1 to 6 from 250 mg of polymers or of polymer mixture are administered in a single dose, of 2 000 IU for standard heparin or 600 IU for LMWH, to rabbits fasted for 12 hours. Blood samples (500 µl) are taken at time $T_0$ and at regular times from the external vein of the ear. After centrifugation of each blood sample at 7 000 g for 8 minutes, the activated cephalin time or the anti-Xa activity are determined as indicated in example 8.

Unexpectedly, as a single oral administration, and with a concentration of active principle that is from 20 to 250 times lower than those used in the prior art [2 000 IU of heparin, whereas the other studies published state doses ranging from 40 000, 60 000 to 90 000 every 8 hours for 5 days (Baugham, Proceed. Intern. Symp. Control. Rel. Bioact. Mater., 26, (1999), 4) up to 500 000 IU (Ueno et al., Chem. Pharm., 30 (6), (1982), 2245-2247)], the heparin particles prepared according to the present invention produce a significant and sustained increase in the clotting time.

In contrast, after oral administration of microparticles or nanoparticles prepared from biodegradable polymers alone (PLGA, PCL, etc.), no absorption of standard heparin was observed. After oral administration of microparticles or nanoparticles prepared from nonbiodegradable polymers alone (Eudragit® RL, Eudragit® RS), no absorption of standard heparin was observed.

Thus, the heparin particulate vectors of the present invention allow the oral administration of doses that are virtually equivalent to those currently administered intravenously and subcutaneously in man, while at the same time ensuring sustained efficacy of the active principle.

EXAMPLE 10

Preparation of Particulate Vectors Containing Insulin (Nanoparticles)

The insulin solution is emulsified using an ultrasound probe for 30 seconds in a solution of dichloromethane containing the polymer mixture (250 mg).

This first water/oil emulsion is then poured into a volume of water (40 ml) containing a surfactant, polyvinyl alcohol (0.1%) and emulsified using an ultrasound probe for 1 minute, thus giving a second water/oil/water emulsion.

The organic solvent is then evaporated off using an evaporator under reduced pressure, resulting in the formation of nanoparticles. The colloidal suspension is centrifuged for 30 minutes (42 000 g), the supernatant is removed and the nanoparticles are resuspended in water and used as obtained. The particles have a mean size of 350 nm.

EXAMPLE 11

Figure 3:
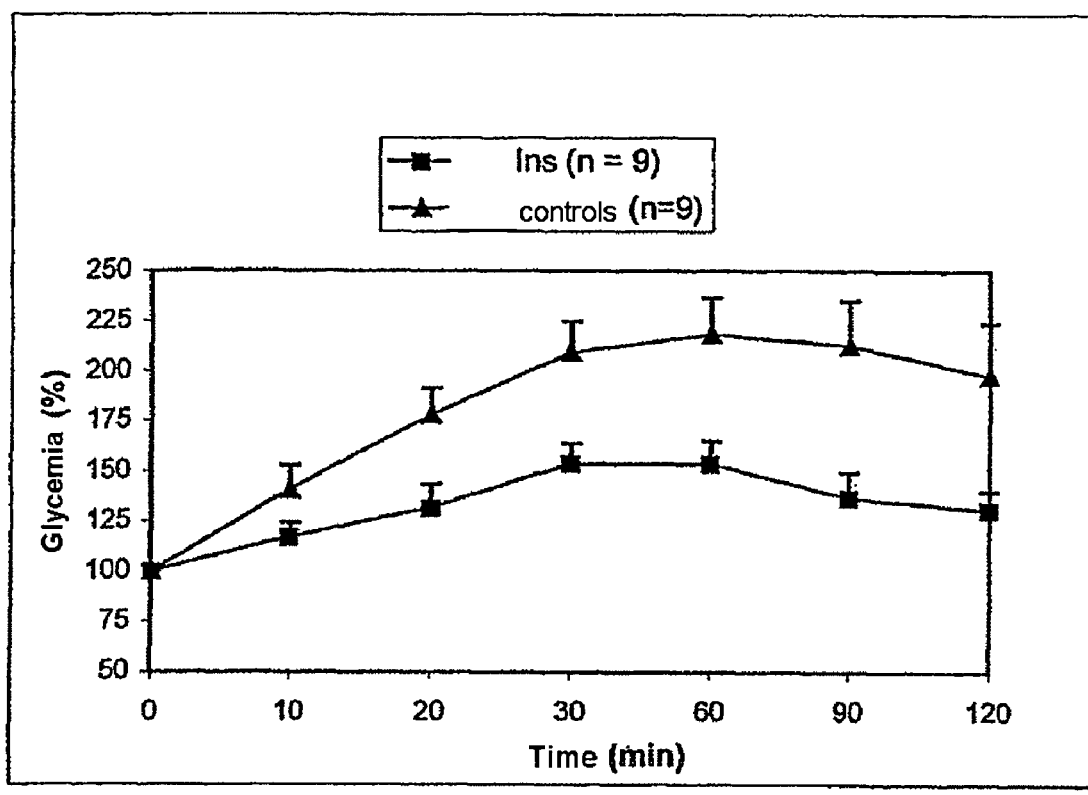
FIG. 3 illustrates the kinetics of glycemia induced with an oral administration of 2 g of glucose, 4 hours after the oral administration of insulin nanoparticles prepared according to the procedure of example 10 (controls=untreated rats; ins=rats treated with nanoparticles according to the invention).
Figure 4:
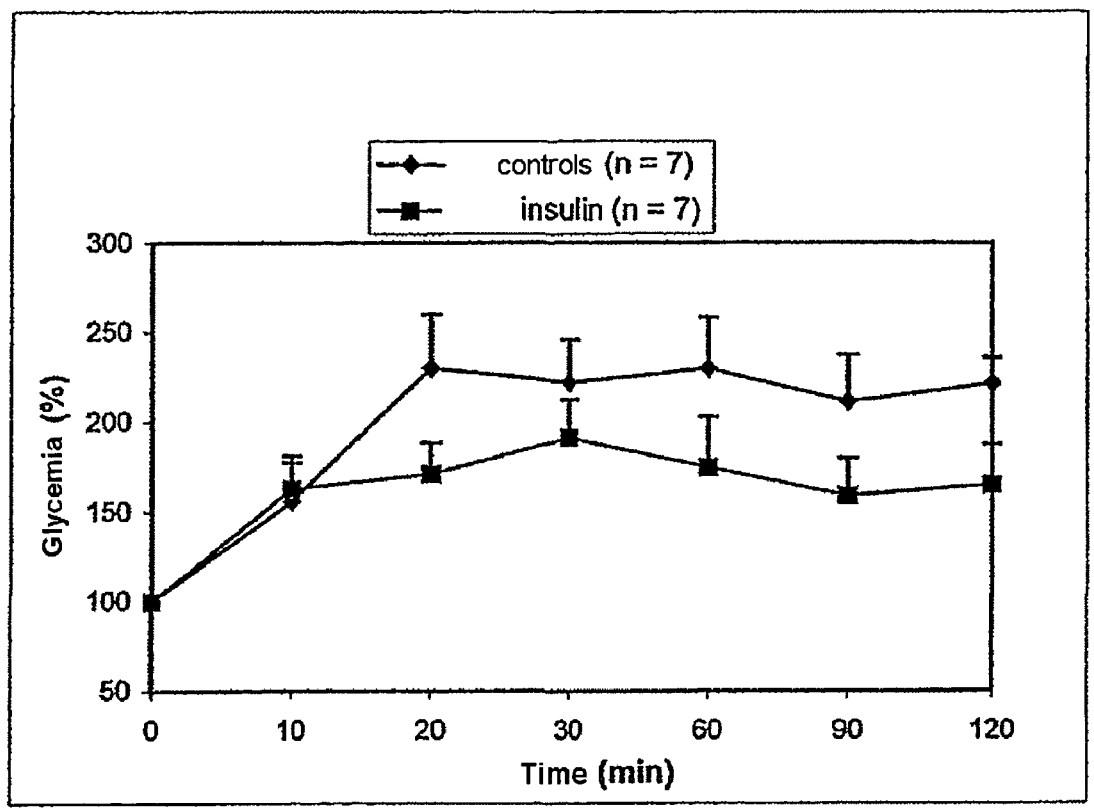
FIG. 4 illustrates the kinetics of the glycemia induced with an oral administration of 2 g of glucose, 8 hours after the oral administration of insulin nanoparticles prepared according to the procedure of example 10 (controls=untreated rats; ins=rats treated with nanoparticles according to the invention).

In Vivo Study After Oral Administration of Insulin Nanoparticles to Diabetic Rats The results are represented by FIGS. 3 and 4.

The suspension of insulin nanoparticles prepared according to example 10 is administered orally as a single dose (100 IU/kg) to rats, fasted for 12 hours, rendered diabetic by administration of streptozotocin. A test of induced hyperglycemia (2 g of glucose administered orally) is performed 4 and 8 hours after oral administration of the nanoparticles. Blood samples are taken at time $T_0$ and at regular times from the vein of the tail. The glycemia and the insulinemia are determined for each blood sample.

Unexpectedly, after a single oral administration, the insulin particles prepared according to the present invention significantly reduce the glycemia.

In parallel, an increase in the insulinemia is observed.

We claim:
1. An oral particulate vector with improved absorption of one or more active principles following oral administration of the particulate vector to a subject in need thereof, wherein the particulate vector comprises at least one active principle and a polymeric matrix comprising a mixture of at least one biodegradable polymer and at least one non-water soluble polycationic polymer, wherein:
the biodegradable polymer is selected from the group consisting of polyesters, lactic acid polymers, copolymers of lactic acid and of glycolic acid (PLGA), poly-ϵ-caprolactone (PCL), polyanhydrides, poly(amides), poly(urethanes), poly(carbonates), poly(acetals), and poly(ortho-esters);

the non-water soluble polycationic polymer is selected from the group consisting of polycationic chitosan, polycationic polylysine and the polycationic copolymers of acrylic and methacrylic acid esters with trimethylammonioethyl methacrylate chloride;

the biodegradable polymer and the polycationic polymer are present in equivalent amounts;

the active principle is selected from the group consisting of insulin, heparin, low molecular weight heparin and heparin with a molecular weight between 2,500 D and 40,000 D; and the biodegradable polymer and the polycationic polymer are non-enteric.

2. The particulate vector of claim 1, wherein the vector is in the form of nanoparticles or microparticles.

3. The particulate vector of claim 1, wherein the vector further comprises one or more substances selected from the group consisting of enteric polymers and water-soluble or liposoluble substances.

4. A pharmaceutical composition comprising at least one particulate vector according to claim 1, in combination with any pharmaceutically acceptable excipient.

5. The pharmaceutical composition of claim 4, wherein the composition allows for the oral administration of standard heparin at a dose of between 2 000 IU and 20 000 IU/day or of LMWH at a dose of between 600 IU and 4 200.

6. The particulate vector of claim 1 comprising at least one active principle encapsulated within a polymeric matrix comprising a mixture of at least one biodegradable polymer and at least one non-water soluble polycationic polymer.

7. The particulate vector of claim 1 comprising a polymeric matrix comprising at least one active principle, and a mixture of at least one biodegradable polymer and at least one non-water soluble polycationic polymer.

8. The particulate vector of claim 1, 6 or 7, wherein the vector has a surface potential in the range of −17.3±1.35 mV to −37.2±3.3 mV.

9. The particulate vector of claim 8, wherein the vector has a surface potential of −17.3±1.35, −20±0.67, −29.9±0.39, −30.7±2.02, −33.6±1.93, −37.2±3.30.

10. The particulate vector of claim 8 comprising:
a) a copolymer of methacrylic acid polyesters with a proportion of trimethylammonioethyl methacrylate chloride, and a copolymer of lactic acid and of glycolic acid;
b) a copolymer of lactic acid and of glycolic acid;
a copolymer of methacrylic acid polyesters with a proportion of trimethylammonioethyl methacrylate chloride, and poly-ϵ-caprolactone; or
c) poly-ϵ-caprolactone.

11. The particulate vector of claim 1, 6, or 7 comprising:
a) a copolymer of methacrylic acid polyesters with a proportion of trimethylammonioethyl methacrylate chloride, and a copolymer of lactic acid and of glycolic acid;
b) a copolymer of lactic acid and of glycolic acid;
a copolymer of methacrylic acid polyesters with a proportion of trimethylammonioethyl methacrylate chloride, and poly-ϵ-caprolactone; or
c) poly-ϵ-caprolactone.

12. An oral particulate vector with improved absorption of one or more active principles following oral administration of the particulate vector to a subject in need thereof, the particulate vector comprising at least one active principle and a polymeric matrix comprising a mixture of at least one biodegradable polymer and at least one non-water soluble polycationic polymer, wherein the biodegradable polymer is selected from the group consisting of polyesters, lactic acid polymers, copolymers of lactic acid and of glycolic acid (PLGA), poly-ϵ-caprolactone (PCL), polyanhydrides, poly(amides), poly(urethanes), poly(carbonates), poly(acetals), and poly(ortho-esters);

the non-water soluble polycationic polymer is selected from the group consisting of polycationic chitosan, polycationic polylysine and the polycationic copolymers of acrylic and methacrylic acid esters with trimethylammonioethyl methacrylate chloride;

the biodegradable polymer and the polycationic polymer are present in equivalent amounts;

the biodegradable polymer and the polycationic polymer are non-enteric;

the active principle is selected from the group consisting of insulin, heparin, low molecular weight heparin and heparin with a molecular weight between 2,500 D and 40,000 D; and the at least one active principle is encapsulated within the polymeric matrix.

13. The particulate vector of claim 12, wherein the vector has a surface potential in the range of −17.3±1.35 mV to −37.2±3.3 mV.

14. The particulate vector of claim 12 comprising:
a) a copolymer of methacrylic acid polyesters with a proportion of trimethylammonioethyl methacrylate chloride, and a copolymer of lactic acid and of glycolic acid;
b) a copolymer of lactic acid and of glycolic acid;
a copolymer of methacrylic acid polyesters with a proportion of trimethylammonioethyl methacrylate chloride, and poly-ϵ-caprolactone; or
c) poly-ϵ-caprolactone.

15. The particulate vector of claim 12 or 13, wherein the vector has a surface potential of −17.3±1.35, −20±0.67, −29.9±0.39, −30.7±2.02, −33.6±1.93, −37.2±3.30 mV.

* * * * *

UNITED STATES PATENT AND TRADEMARK OFFICE
CERTIFICATE OF CORRECTION

PATENT NO. : 8,052,998 B2  
APPLICATION NO. : 10/332351  
DATED : November 8, 2011  
INVENTOR(S) : Philippe Maincent, Nathalie Ubrich and Claude Vigneron Page 1 of 1

It is certified that error appears in the above-identified patent and that said Letters Patent is hereby corrected as shown below:

On the Title page, Item (73):

The Assignee should be "Laboratorios Farmaceuticos Rovi, S.A."

Signed and Sealed this  
Twenty-fourth Day of January, 2012

David J. Kappos  
*Director of the United States Patent and Trademark Office*